(12) United States Patent
Buchberger

(10) Patent No.: US 10,701,969 B2
(45) Date of Patent: Jul. 7, 2020

(54) INHALER COMPONENT

(71) Applicant: BATMARK LIMITED, London (GB)

(72) Inventor: Helmut Buchberger, Ennsdorf (AT)

(73) Assignee: BATMARK LIMITED, London (GB)

( * ) Notice: Subject to any disclaimer, the term of this patent is extended or adjusted under 35 U.S.C. 154(b) by 0 days.

(21) Appl. No.: 15/399,121

(22) Filed: Jan. 5, 2017

(65) Prior Publication Data

US 2017/0112190 A1  Apr. 27, 2017

Related U.S. Application Data

(63) Continuation of application No. 13/583,365, filed as application No. PCT/AT2010/000122 on Mar. 10, 2011, now Pat. No. 9,554,595.

(30) Foreign Application Priority Data

Mar. 10, 2010 (AT) .................................. A 385/2010

(51) Int. Cl.
  *A24F 47/00* (2020.01)
  *A61M 15/06* (2006.01)
  *A24F 7/02* (2006.01)

(52) U.S. Cl.
  CPC .............. *A24F 47/002* (2013.01); *A24F 7/02* (2013.01); *A61M 15/06* (2013.01)

(58) Field of Classification Search
  CPC ............................. A24F 47/002; A24F 47/004
  See application file for complete search history.

(56) References Cited

U.S. PATENT DOCUMENTS

| | | | |
|---|---|---|---|
| 2,809,634 A | 10/1957 | Murai | |
| 3,356,094 A * | 12/1967 | Ellis et al. | A24F 47/004 |
| | | | 131/273 |
| 3,521,642 A | 7/1970 | Toth | |
| 3,521,643 A | 7/1970 | Toth | |
| 4,094,119 A | 6/1978 | Sullivan | |
| 4,145,001 A | 3/1979 | Weyenberg | |
| 4,161,283 A | 7/1979 | Hyman | |
| 4,480,647 A * | 11/1984 | Sprecker et al. | A24B 15/34 |
| | | | 131/276 |
| 4,503,851 A | 3/1985 | Braunroth | |

(Continued)

FOREIGN PATENT DOCUMENTS

| | | |
|---|---|---|
| CN | 2487392 | 4/2002 |
| CN | 101137446 | 3/2008 |

(Continued)

OTHER PUBLICATIONS

Application and File History for U.S. Appl. No. 15/503,456, Inventor: Buchberger, filed Feb. 13, 2017.

(Continued)

*Primary Examiner* — Michael H. Wilson
*Assistant Examiner* — Dionne W. Mayes
(74) *Attorney, Agent, or Firm* — Patterson Thuente Pedersen, P.A.

(57) ABSTRACT

The disclosure relates to an inhaler component including a housing with a housing cover; a mouthpiece with a mouthpiece opening for supplying an inhalable medium into the oral cavity of a user; and a flavor reservoir communicable with the environment by diffusion, containing a flavor, wherein the flavor reservoir is formed from a porous body.

18 Claims, 13 Drawing Sheets

(56) References Cited

U.S. PATENT DOCUMENTS

| | | | |
|---|---|---|---|
| 4,917,301 A | 4/1990 | Munteanu | |
| 4,947,874 A | 8/1990 | Brooks | |
| 5,167,242 A * | 12/1992 | Turner et al. | A24F 47/002 |
| | | | 128/202.21 |
| 5,301,694 A * | 4/1994 | Raymond et al. | A24B 15/24 |
| | | | 131/199 |
| 5,388,594 A | 2/1995 | Counts | |
| 5,501,236 A | 3/1996 | Hill | |
| 5,636,787 A | 6/1997 | Gowhari | |
| 5,799,663 A * | 9/1998 | Gross et al. | A24F 47/002 |
| | | | 131/270 |
| 6,155,268 A | 12/2000 | Takeuchi | |
| 7,100,618 B2 | 9/2006 | Dominguez | |
| 7,647,932 B2 | 1/2010 | Cantrell | |
| 8,430,106 B2 * | 4/2013 | Potter et al. | A24F 47/004 |
| | | | 131/194 |
| 8,459,271 B2 | 6/2013 | Inagaki | |
| 8,997,753 B2 | 4/2015 | Li | |
| 9,167,852 B2 | 10/2015 | Xiu | |
| 9,532,597 B2 | 1/2017 | Tucker | |
| 9,642,397 B2 | 5/2017 | Dai | |
| 9,814,262 B2 | 11/2017 | Peleg | |
| 9,814,263 B2 | 11/2017 | Cochand | |
| 9,861,772 B2 | 1/2018 | Terry | |
| 2006/0054165 A1 | 3/2006 | Hughes | |
| 2006/0196518 A1 | 9/2006 | Hon | |
| 2007/0023056 A1 | 2/2007 | Cantrell | |
| 2007/0062548 A1 | 3/2007 | Horstmann | |
| 2008/0110458 A1 | 5/2008 | Srinivasan | |
| 2008/0241255 A1 | 10/2008 | Rose | |
| 2009/0272379 A1 * | 11/2009 | Thorens et al. | A24F 47/008 |
| | | | 128/202.21 |
| 2011/0226236 A1 | 9/2011 | Buchberger | |
| 2011/0290267 A1 | 12/2011 | Yamada | |
| 2011/0297166 A1 | 12/2011 | Takeuchi | |
| 2017/0112889 A1 | 4/2017 | Spencer | |
| 2017/0238611 A1 | 8/2017 | Buchberger | |

FOREIGN PATENT DOCUMENTS

| | | |
|---|---|---|
| CN | 103393222 A | 11/2013 |
| DE | 19630619 | 2/1998 |
| DE | 19654945 | 3/1998 |
| DE | 10 2006 039115 | 3/2008 |
| EP | 0150810 A2 | 8/1985 |
| EP | 0 836 857 | 4/1998 |
| EP | 2 481 308 A1 | 8/2012 |
| EP | 2625974 A1 | 8/2013 |
| GB | 408856 | 4/1934 |
| JP | 62-175896 | 11/1987 |
| JP | 1-94861 | 4/1989 |
| JP | 7-184627 | 7/1995 |
| JP | 8-56640 | 3/1996 |
| JP | 11-9693 | 1/1999 |
| JP | 2002-078476 | 3/2002 |
| WO | WO 88/01884 | 3/1988 |
| WO | WO 96/22801 | 8/1996 |
| WO | WO 98/28994 A1 | 7/1998 |
| WO | WO2003034847 A1 | 5/2003 |
| WO | WO 2006/086655 | 8/2006 |
| WO | WO2007039794 A2 | 4/2007 |
| WO | WO 2008/108889 A1 | 9/2008 |
| WO | WO 2009/135729 A1 | 11/2009 |
| WO | WO 2010/045670 A1 | 4/2010 |
| WO | WO 2010/095659 | 8/2010 |
| WO | WO 2010/095660 | 8/2010 |
| WO | WO 2011/109848 A1 | 9/2011 |
| WO | WO 2013/050934 A1 | 4/2013 |
| WO | WO2014097294 A1 | 6/2014 |
| WO | WO 2014/110119 A1 | 7/2014 |
| WO | WO 2014/140273 A2 | 9/2014 |
| WO | WO 2016/005533 A1 | 1/2016 |
| WO | WO 2017/109448 | 6/2017 |

OTHER PUBLICATIONS

International Search Report, Application No. PCT/AT2011/000122, dated Aug. 4, 2011, 6 pages.
Application and File History for U.S. Appl. No. 13/583,365, Inventor: Buchberger, filed Oct. 23, 2012, filed Oct. 23, 2012.
GB Search Report, GB Application No. GB1414331.7, dated Feb. 2, 2015, 4 pages.
International Search Report and Written Opinion, International Application No. PCT/GB2015/052212, dated Oct. 21, 2015, 19 pages.
International Preliminary Report on Patentability, International Application No. PCT/GB2015/052212, dated Nov. 29, 2016, 16 pages.
EPO Office Action, Application No. 15747208.8, dated Dec. 4, 2017, 8 pages.
McNeil Consumer Healthcare GMBH, Nicorette® Inhaler, available at www.nicorette.de, as retrieved on Apr. 17, 2018, 8 pages.
Celgard LLC, World Leader in Battery Separator Technology, available at www.celgard.com, as retrieved on Apr. 17, 2018, 6 pages.
Mitsubishi Materials Corporation, available at http://www.mmc.co.jp/corporate/en, as retrieved on Apr. 17, 2018, 5 pages.
Freudenberg Vliesstoffe KG, Vildeon® Filter Mats, available at https://www.freudenberg-filter.com/company/brands/viledon/, as retrieved on Apr. 17, 2018, 2 pages.
Japan Tobacco Inc., ZeroStyle®, available at www.jt.com, as retrieved on Apr. 17, 2018, 7 pages.
Red Arrow International LLC, available at www.redarrowinternational.com, as retrieved on Apr. 17, 2018, 1 page.
Porex Technologies, Porex Custom Plastics, as available at www.porex.com, as retrieved on Apr. 17, 2018, 2 pages.
Russian Office Action, Application No. 2017104461, dated Apr. 28, 2018, 6 pages (10 pages with translation).
Korean Office Action, Application No. 10-2017-7003991, dated Apr. 6, 2018, 8 pages (15 pages with translation).
Japanese Office Action, Application No. 2017-507765, dated Jan. 30, 2018, 5 pages (10 pages with translation).
Korean Office Action, Application No. 10-2017-7003991, dated Oct. 29, 2018, 7 pages (13 pages with translation).
Chinese Office Action, Application No. 201580043507.8, dated Nov. 5, 2018, 5 pages.

* cited by examiner

INHALER COMPONENT

CROSS REFERENCE TO RELATED APPLICATIONS

This application is a continuation of application Ser. No. 13/583,365 filed Oct. 23, 2012, which in turn is a 35 U.S.C. § 371 National Phase conversion of PCT/AT2010/000122, filed Mar. 10, 2011, which claims benefit of Austrian Patent Application No. A 385/2010, filed Mar. 10, 2010, the disclosure of which is incorporated herein by reference. The PCT International Application was published in the German language.

TECHNICAL FIELD

The invention relates to an inhaler component.

BACKGROUND

In the present patent application the term "inhaler" refers to medical as well as non-medical inhalation device. The term refers in addition to cigarette substitutes, as disclosed, for example, in European patent class A24F47/00B, in so far as these are intended to provide the user with an inhalable medium. The inhalable medium consists of a vapor-air mixture and/or an aerosol, in particular of a nicotine-containing vapor-air mixture and/or aerosol. The use of the singular "flavor" is not to suggest that the flavor consists of only one ingredient. Rather the "flavor" can also contain a large number of very different individual substances. Any reservoir can be considered a "flavor reservoir communicable with the environment by diffusion" if the 1 flavor which it contains can volatilize into the environment by evaporation and/or sublimation and diffusion.

Currently available nicotine inhalers are usually designed in such a way that they dispense a nicotine-containing vapor-air mixture and/or aerosol into the oral cavity of a user. As an example, mention may be made of the nicotine inhaler sold by McNeil Consumer Healthcare GmbH under the designation "Nicorette® Inhaler", cf. www.nicorette.de. This inhaler supplies a nicotine-containing vapor-air mixture to the user by way of a mouthpiece, the organoleptic effects of which many users find unpleasant. In no way is this inhaler able to copy the complex organoleptic effects of cigarette smoke. Stimulation of an olfactory appeal, like that caused by sidestream smoke flowing from the glowing end of the cigarette during the course of smoking a cigarette, is completely lacking. One can assume from this that this additional olfactory stimulus is to be equated with a key attraction which gives cigarette smokers a substantial incentive to maintain their tobacco consumption.

U.S. Pat. No. 7,100,618 (Armando Dominguez) describes a sensory smoke simulator, consisting of a housing 40, which contains two chambers 41, 42 separated by a partition 43. The lower chamber 42 is provided with an air intake window 10 on one side. On the opposite side it is connected with a tubular mouthpiece holder 14a. The tubular mouthpiece holder 14a holds a mouthpiece 15 with an internal passage 14b. The mouthpiece 15 exhibits a bitter taste similar to that of cigarette smoke. In the lower chamber 42 two impellers 12 are arranged which are caused to rotate by the suction current caused by the user in the course of inhaling. The impellers 12 for their part drive via shafts 16 two corresponding impellers 29 arranged in the upper chamber 41, which work like a suction pump. The upper chamber 41 has a cigarette holder 24 on one side. On the opposite side are two discharge opening tubes 30 connected to the chamber 41 and arranged in such a way that during use of the smoking simulator their openings lie in the proximity of the nose of the user. The upper chamber 41 is closed by a cover 34. A main discharge opening 35 is integrated into the cover 34. To operate the smoking simulator: the user inserts a cigarette 21a into the cigarette holder 24 and lights it. As soon as inhalation is effected via the mouthpiece 15, the impellers 12 are set in motion and in turn drive the suction pump impellers 29. The latter cause air from the environment to be drawn through the cigarette 21a and in the course of this, as when smoke forms when a conventional cigarette is smoked, the smoke is pumped through the chamber 41. The predominant part of the smoke is again blown out unused into the environment via the main discharge opening 35, while a smaller quantity of the smoke leaks out intentionally via the discharge opening tubes 30 into the proximity of the nose of the user, who detects the tobacco smoke flavor. In an alternative arrangement of the smoke simulator, bodies 21e impregnated with cigarette smoke flavor be can also inserted into the cigarette holder 24 (FIG. 3A) instead of the cigarette 21a. In a further alternative arrangement an electric motor 17 can also propel the suction pump impellers 29 instead of the impellers 12 (FIG. 2).

The inertia of the four impellers 12, 29, the friction in their bearings, the gaps between the impellers and the housing 40 and the dead volumes always existing in the chambers 41, 42 have the consequence that gas volume (approx. 20-80 mL) usually sucked into the oral cavity during a draw when smoking a cigarette will probably not be sufficient to effect a function as previously described. Apart from this, the smoke simulator has a quite complicated and complex structure. The cost of manufacture is also not reduced if the impellers 12 are replaced with an electric motor 17. In using the cigarette 21a substantial quantities of sidestream smoke injurious to health are formed and released into the environment. No more detailed information is provided about the ingredients of this body 21e impregnated with "cigarette smoke flavor". JP 11-009693 (Nagai Kenichi) shows an arrangement which is similar in principle.

JP 08-056640 (Setsuo Kuroki) describes inhalation device, essentially consisting of (FIGS. 3, 4 and 6) a drum 7, containing a body 6 impregnated with flavor or a body 6a impregnated with tobacco smoke flavor and furthermore consisting of a mouthpiece unit 10 with a mouthpiece 11. In the front part of the device is a first check valve B, which opens and closes an entrance opening 3. In the rear part of the device is a second check valve C, which opens and closes an outlet 15. The function of the device is shown in FIG. 7: during a draw and/or an inhalation, air from the environment flows into the device via the entrance opening 3, permeates the body 6 impregnated with flavor and/or the body 6a impregnated with tobacco smoke flavor, is enriched with flavor and finally arrives in the oral cavity of the user via the mouthpiece 11. The air-flavor mixture administered in this way is not exhaled into the environment after inhalation, as is usual with cigarettes, but is blown back into the inhalation device via the mouthpiece 11, as a result of which a positive pressure develops in the device. The positive pressure causes the check valve C to open and the air-flavor mixture leaks out in the direction of the nose of the user via the outlet 15, whereby the air-flavor mixture can finally be smelt by the user. A cigarette smoker would thus have to change his draw and/or inhalation behavior completely if he wanted to use this inhalation device. This circumstance is to be considered as a disadvantage. Furthermore, it is considered as unfavorable that stimulation of olfactory appeal does not take place at the same time as the draw. No further detail is provided on the ingredients of the flavor administered and/or "tobacco smoke flavor". JP 01-094861 (Watabe Isamu) shows an arrangement operating on a similar principle, which operates without the use of check valves.

U.S. Pat. No. 2,809,634 (Hirotada Murai) and GB 408, 856 (Wietske van Seters-Bosch et al.) describe inhalation apparatuses which enable the simultaneous inhalation of an inhalable medium by mouth and nose. The device in accordance with U.S. Pat. No. 2,809,634 relates to a very complex construction, where the inhalable medium can be drawn after manipulation of a valve mechanism by the user, where the manipulation of the valve mechanism is effected by the clamping together of the teeth. In the case of GB 408,856 the user must employ two nasal tubes as well as a mouthpiece. Many users have rejected these devices simply on the grounds of their strange handling and operation, which has limited social acceptability. According to U.S. 2,809,634 the inhalable medium can be a tobacco extract or tobacco smoke extract dissolved in alcohol. Ether is cited by way of example as a solvent for the extraction.

WO 88/01884 (Paul Terasaki) describes different variants of a "sniffing stick", which in total comprises: a mouthpiece 1, an extension 2 and an odoriferous substance preparation 3, which is supported by the extension 2. If a user holds the mouthpiece 1 between his lips or teeth, the odoriferous substance preparation 3 is in the proximity of his nostrils, so that the odoriferous substances can be consumed in an efficient way. In the example in accordance with FIG. 4, a single plastic rod forms both the mouthpiece 1 and the extension 2. The odoriferous substance preparation 3 is absorbed in a paper substrate 4, which is wound around the extension 2 and is fixed to the plastic rod by means of an adhesive. FIG. 7 shows in principle a similar arrangement; the main difference is that in the example in accordance with FIG. 7 both the mouthpiece 1 and the extension 2 are flat. FIGS. 8 and 9 show arrangements with an angled extension 2. These variants have the effect that the odoriferous substance-soaked substrate 4 moves even closer to the user's nostrils during use. FIGS. 11-37 show arrangements with rod-shaped substrates 4, which are arranged in cavities 8 formed of cylindrical extensions 2. Various control devices are envisaged, by means of which the user can exert an influence within certain limits on the release of the odoriferous substances. WO 88/01884 discloses a "sniffing stick" for the exclusive administration of odoriferous substances into the nose of a user, but there is no reference to inhalers and consequently it cannot impart any concrete teachings to the skilled man as to how an odoriferous substance substrate could advantageously be integrated into an inhaler arrangement.

U.S. Pat. No. 4,503,851 (Klaus Braunroth) describes a one-way protective mask for the masking of unpleasant smells for use in a foul-smelling environment, for example in the environment of animal wastes. The protective mask 40 is based on (FIG. 5-7) an air-permeable, filtering fabric cover 41, which can be secured to the head by means of straps 42. For instance, in the centre of the fabric cover 41 there is an odor-masking means 50, consisting of an impermeable covering 52. The covering 52 consists of two mutually opposing surfaces 52A and 52B. Between the surfaces 52A and 52B there is an absorbing material 54, e.g. cotton. The absorbing material 54 is impregnated with an odor-masking substance 55. The surface 52B is provided with a multiplicity of openings 56 and is overlaid with a seal 60, which is stuck together at the outside margin of the covering 52. The seal 60 exhibits a latch 62, by means of which the seal 60 can be removed from the covering 52. After removal of the seal 60, the protective mask 40 is operational. The odor-masking substance 55 can now evaporate through the openings 56 and mix with the odor-laden air flowing through the fabric cover 41 and neutralize any odor.

Finally it should be noted that the state of the art disclosed in the above-described documents does not formally include the type designated in the preamble. Nevertheless, the aforementioned documents are cited, since they at least illustrate the further environment of the invention which is the subject of the present application and are, to that extent, worthy of consideration.

SUMMARY

It is the task of the invention to remedy the aforementioned disadvantages of the state of the art. A particular object of the invention is to provide an inhaler component of the afore-mentioned type such that the flavor is dispensed in an efficient manner and uninvolved third parties are troubled as little as possible by the release of the flavor; the whole arrangement of the inhaler component remains compact; the inhaler component is user-friendly, ergonomic and simple to handle, and its use is hygienic; the olfactory effects of cigarette sidestream smoke is copied as realistically as possible.

This task is solved in that a) the housing comprises a housing component;

b) the mouthpiece is separably connected to the housing component;

c) the housing cover comprises a first cover component and a second cover component;

d) the housing component forms the first cover component;

e) the mouthpiece forms the second cover component;

f) and the flavor reservoir is structurally united with the mouthpiece, is superficial and is arranged superficially on the second cover component or itself forms the second cover component.

The use of the singular "flavor reservoir" is not to exclude the presence of several flavor reservoirs. It is also expressly considered as in accordance with the invention that several flavor reservoirs are present. The superficial, e.g. plate or dish-shaped design, of the flavor reservoir and its superficial arrangement on the housing cover and/or integration into the housing cover has the effect that, on the one hand, different functional parts within the housing cover, in particular functional parts for the formation of the inhalable medium, are not or are not substantially affected in their arrangement and, on the other hand, the flavor reservoir attaches smoothly or approximately smoothly to neighboring housing sections, which is not only considered an advantage from an aesthetic viewpoint, but also simplifies the handling of the inhaler component. Practical examples of flavor reservoirs, in particular for plate-shaped flavor reservoirs, will be shown hereinafter.

By arranging the flavor reservoir on the second cover component formed on the mouthpiece and/or by designing the second cover through the flavor reservoir, the flavor reservoir comes to lie close to the user's nostrils when the inhaler component is used. The flavor released under these conditions can be detected by the user even with comparatively low release rates, where the perception is still further supported by nasal respiration and the convective material transfer additionally induced thereby. Other persons in the closer environment are hardly affected by the flavor released because of the very much greater distance to the flavor reservoir. By the structural combination of the flavor reservoir with the replaceable mouthpiece it is possible to exchange both construction units together. This substantially simplifies handling. The handling is very easy: the user takes the free mouthpiece end and detaches the mouthpiece from the housing component. In this way he does not come into contact with the flavor reservoir. It is particularly advantageous if the flavor reservoir is inseparably connected to the mouthpiece. The user is thus actually compelled to replace the mouthpiece regularly by a new mouthpiece if he wishes to maintain the flavor release. The regular, e.g. daily, exchange of the mouthpiece is undoubtedly advantageous from a hygienic point of view.

In an advantageous further embodiment of the invention it is intended that the first cover component and the second cover component at least partly overlap in the region of the flavor reservoir and/or its surrounding area. Furthermore, in a particularly advantageous embodiment of the invention, it is intended that the flavoring reservoir and/or the flavor reservoir cover section of the second cover component at least partly engages in a recess or recess in the first cover component, or the flavor reservoir communicates with the environment via a recess in the first cover component. This arrangement gives the technical designer more flexibility in the positioning of the flavor reservoir on the housing cover and allows nesting with other functional devices, so that the inhaler component can in the long run be built even more compactly.

In accordance with the invention the mouthpiece opening and the flavor reservoir are arranged on opposite sides of a housing centre plane m, where the housing centre plane m is defined as a plane which divides the housing in the cover direction into two approximately equal-sized parts. This arrangement has the effect that the flavor reservoir is brought even closer to the nostrils of the user during use of the inhaler component, so that the flavor can be administered even more efficiently, or to put it another way, the release rate can be further reduced with the same olfactory effect. Finally, the service life of the flavor reservoir can be extended in this way.

In a further embodiment of the invention, the mouthpiece also comprises a cooler, through which the vapor and/or particle phase of the inhalable medium can flow; in another further embodiment the mouthpiece additionally comprises a flavoring reservoir enriching the inhalable medium with flavorings. With these further extensions the mouthpiece is upgraded to a multi-function mechanism, which contains yet another cooler and/or a flavoring reservoir beside the flavor reservoir. All function mechanisms can be exchanged by a simple manipulation. The operation of the inhaler component is thus substantially simplified. The cooler cools the inhalable medium, as a result of which it is consumed more pleasantly. Such cooling has proved very favorable in particular with nicotine-containing vapor-air mixtures and condensation aerosols, if these are formed in suction inhalers by the evaporation of nicotine solutions highly diluted with ethanol and/or water. Suction inhalers are inhalation devices with which the inhalable medium is supplied to the user as with a cigarette in two steps, i.e. first drawn into the oral cavity (first step) and—after removing the inhaler—in the form of a subsequent inhalation into the lungs (second step). The cooler can, for example, take the form of a permeable porous body. The porous body can be additionally flavored. In the latter case, the permeating vapor-air mixture and/or aerosol is not only cooled, but also further enriched with flavorings, so that it is still more pleasant to consume.

Naturally, flavoring reservoirs without, or without significant, cooling effect can also be provided. Thus, for example, the channel walls of the mouthpiece conducting the inhalable medium could be coated with a flavoring material.

It is particularly advantageous if the flavoring reservoir is formed as a reservoir through which ambient air can flow, but which is not subjected to the vapor and/or particle phase of the inhalable medium reservoir. The air flow flowing through the flavoring reservoir is enriched with the flavoring and is finally combined further downstream outside the flavoring reservoir with the main stream carrying the vapor and/or particle phase of the inhalable medium. This arrangement can effectively prevent condensate and/or aerosol particle separation in the flavoring reservoir, which could severely disturb the release of the flavoring.

In accordance with the invention it is provided that the flavor of the flavor reservoir contains tobacco. Suitable tobaccos are, in particular, dried fermented tobacco, reconstituted tobacco, expanded tobacco or mixtures of the same. Since tobacco is a natural raw material, it can probably be assumed that inhaler components or inhalers in accordance with the invention equipped with tobacco-containing flavor reservoirs will be highly acceptable to many users. It is particularly advantageous if the tobacco is present as cut tobacco, preferably fine cut tobacco, or as fine granulates or tobacco flour. The large surface area of these forms of tobacco supports the release of the aromatic materials present in the tobacco.

It is alternatively provided in accordance with the invention that the flavor of the flavor reservoir contains a tobacco smoke condensate or a tobacco extract or a volatile aromatic fraction of the aforementioned material mixtures which is nevertheless essentially free from nicotine. Nicotine itself possesses useful flavor characteristics, which, however, bear no relation to its toxic effects (LD50: 0.88 mg·kg$^{-1}$). Since the flavor reservoir is accessible from the outside, the nicotine content of the aromatic material is limited in accordance with the invention, namely to 0.5% by wt. This residual nicotine content still counts as "nicotine-free" in the context of the present patent application.

The term "tobacco smoke condensate" is to be understood to cover any condensed tobacco smoke. Tobacco smoke condensate has a viscous to paste-like consistency and a yellowish-brown color. By using this as a flavor in a flavor reservoir in accordance with the invention it is possible to copy the important olfactory effects of cigarette sidestream smoke. The production of tobacco smoke condensate has so far taken place primarily for the purposes of analysis in the laboratory yardstick during machine smoking of cigarettes and similar smoking goods. Here the procedures used for the separation of the condensate can be divided into four principles:

1) Separation by baffle effect, e.g. on filters or by means of capillary presses ("Jet Impaction Trap");
2) Separation by means of cooling;
3) Separation in an electrical field;
4) Separation in suitable solvents, e.g. in wash bottles, or precipitation by means of sprayed solvents. Suitable solvents include, in particular, water, acetone and ethanol.

An industrial/commercially used procedure for the production of larger quantities of tobacco smoke condensate is not known to the applicant. However, industrial plants exist for the production of liquid smoke products from wood for use in or on food as a replacement for smoking. An example of an operator of such plants is the company Red Arrow International LLC, www.redarrowinternational.com. The plants are based on the pyrolysis of hardwood sawdust. The sawdust is heated under the substantial exclusion of oxygen and the flue gases produced taken up in solvents such as water. The industrial production of tobacco smoke condensate can take place in similar plants. The raw material to be pyrolysed consists of dried fermented tobacco, whereby tobacco cultivated to be nicotine-free or denicotinised tobacco have the advantage that a nicotine-free tobacco smoke condensate can be obtained without additional process steps.

Tobacco smoke condensates consist of a highly complex mixture of several thousands of individual substances, many of which have aromatic characteristics and to that extent contribute to the overall flavor of the tobacco smoke condensate; others have no or even unfavorable flavor characteristics. The evaporability of all these ingredients is very varied, which leads to the flavor reservoir releasing above-average quantities of readily volatile substances in the initial phase of its use, where the flavor shifts over the service life qualitatively and soon becomes less effective. By suitable refining the ingredients and characteristics of the tobacco smoke condensate can be influenced. In particular, ingredients or fractions without or with unfavorable flavor characteristics can be separated, the evaporability spectrum restricted and the concentration of favorable aromatic components increased. The procedures which can be used for this, such as extraction and distillation, are known to those skilled in flavor and aromachemistry. The final product of the refining is a nicotine-free, volatile, concentrated aromatic fraction of tobacco smoke condensate, or several of such fractions, e.g. fractions with different evaporability spectra.

The term "tobacco extract" is understood as an ethereal oil obtained from fermented tobacco. These oils are also often called "tobacco flavoring oils". The production of nicotine-free tobacco flavoring oils can take place, for example, in procedures set out in detail in the patent publications DE 19654945 and DE 19630619 (Adam Muller et al.). The tobacco flavoring oil can if necessary still be broken down into fractions with different evaporability spectra.

In addition, it is regarded as in accordance with the invention that the flavor in the flavor reservoir contain at least one volatile acid and the total of all volatile acids in the flavor is greater than 5% by weight. The volatile acid in the flavor should provide the user with an odor impression which is similar to the slightly pungent aroma of cigarette sidestream smoke, combined with a comparable irritation of the nasal mucous membrane. Suitable volatile acids are, for example, acetic acid, formic acid and propionic acid, as well as mixtures of the same. The invention is not limited to these acids, however.

Finally it is envisaged in accordance with the invention that the flavor in the flavor reservoir is menthol. Menthol has a refreshing effect. Its addition pleasantly rounds off the complete flavor. The menthol can be added as an individual substance or as a component of an ethereal oil, e.g. peppermint oil.

BRIEF DESCRIPTION OF THE DRAWINGS

Appropriate and advantageous examples of the invention are represented in the drawings and are described in more detail in the following description. These show.

DETAILED DESCRIPTION

Figure 1:
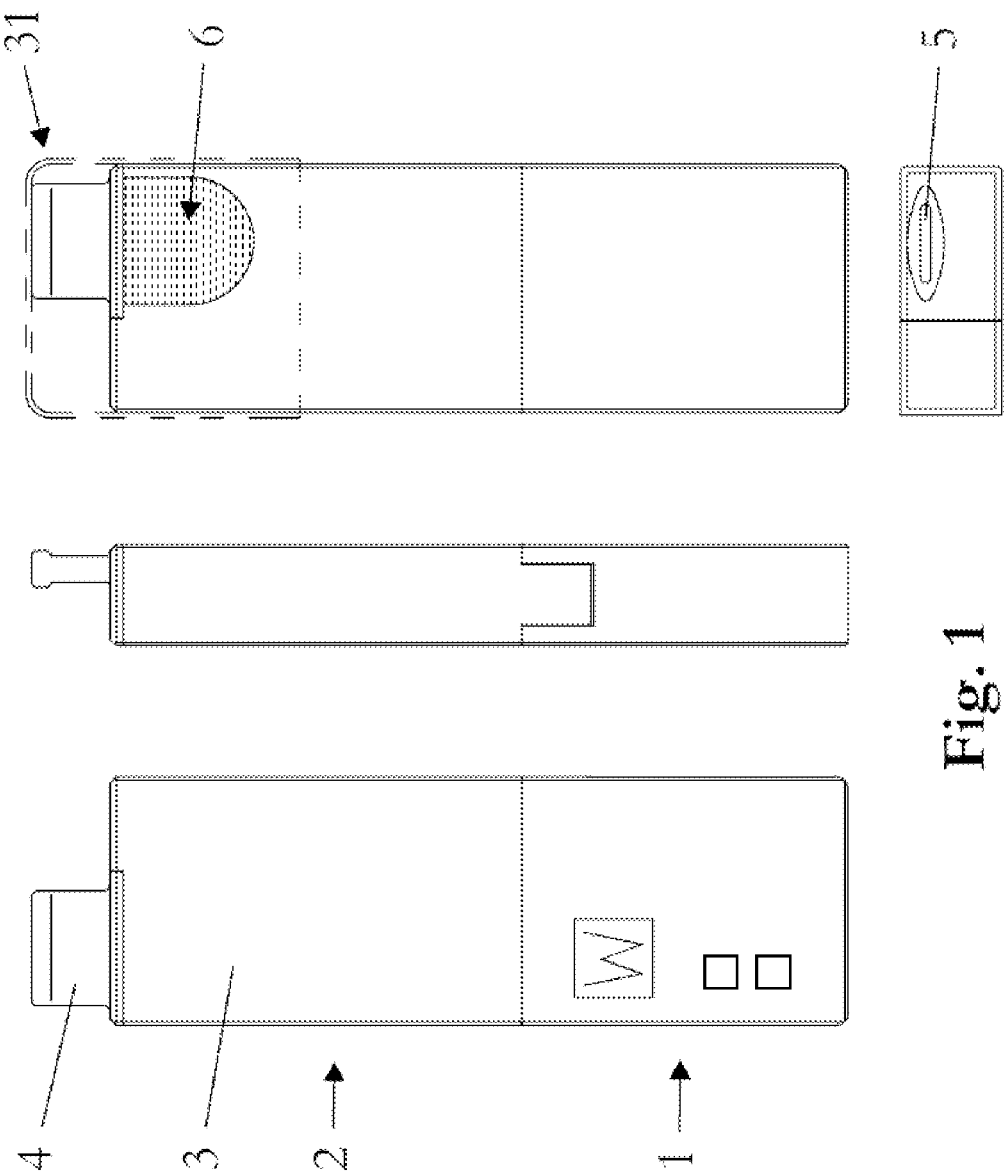
FIG. 1 various views of an inhaler in accordance with the invention.

FIG. 1 shows an example of an inhaler in accordance with the invention, which in this particular case consists of two parts, namely an inhaler component 1 and an inhaler component 2. The inhaler component 2 further comprises a rectangular housing 3. The inhaler component 2 further comprises a mouthpiece 4 with a tobacco pipe-like mouthpiece end and a mouthpiece opening 5 for the supply of an inhalable medium into the oral cavity of a user. Finally, the inhaler component 2 further contains a U-shaped flavor reservoir 6. The flavor reservoir 6 is integrated into the housing cover, as shown later in more detail. The housing 3 and the mouthpiece 4 are preferably made of plastic.

Figure 2:
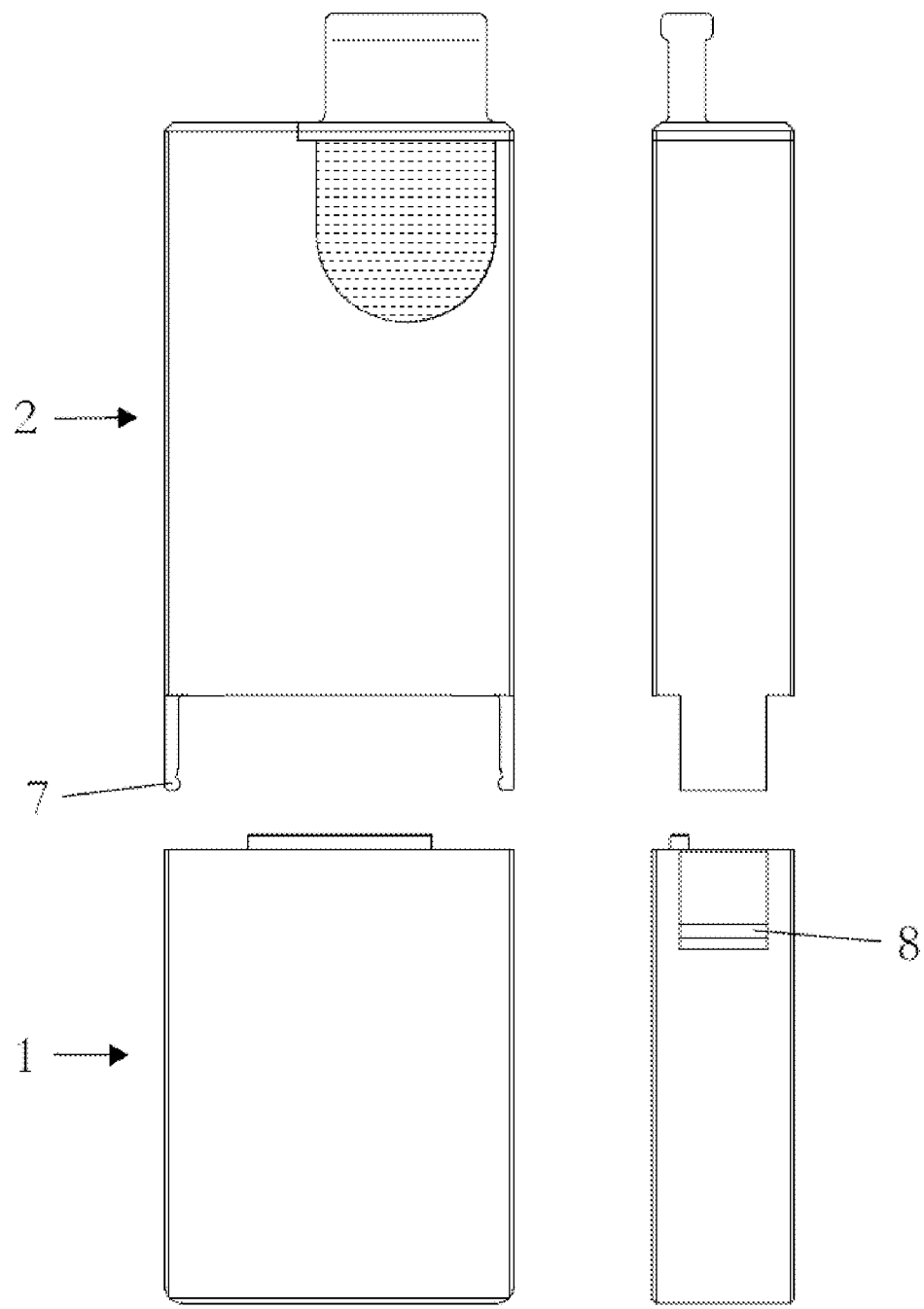
FIG. 2 an inhaler in accordance with FIG. 1 with a re-usable inhaler component and a replaceable inhaler component in the dismantled condition.

As shown in FIG. 2, the inhaler component 1 and the inhaler component 2 are designed to be separable from each other in the present example. The separable coupling consists of a snap connection, formed from two latching hooks 7 and two detents 8 interacting with them. This arrangement makes the inhaler component 1 reusable and/or the inhaler component 2 exchangeable and is particularly advantageously applicable if the inhaler component 1 contains components which are more long-lived than the components of inhaler component 2. Such longer-life components can, for example, be rechargeable batteries as well as electronic circuits. It must be stressed that the invention is in no way limited to this two-piece inhaler concept. The invention is rather applicable to any type of inhaler if it has a mouthpiece for delivering an inhalable medium into the oral cavity of a user. Thus the inhaler component 1 and the inhaler component 2 could naturally also be implemented in one piece and hence be inseparable from each other, where in this case the whole inhaler would be understood as inhaler component 2.

Figure 3:
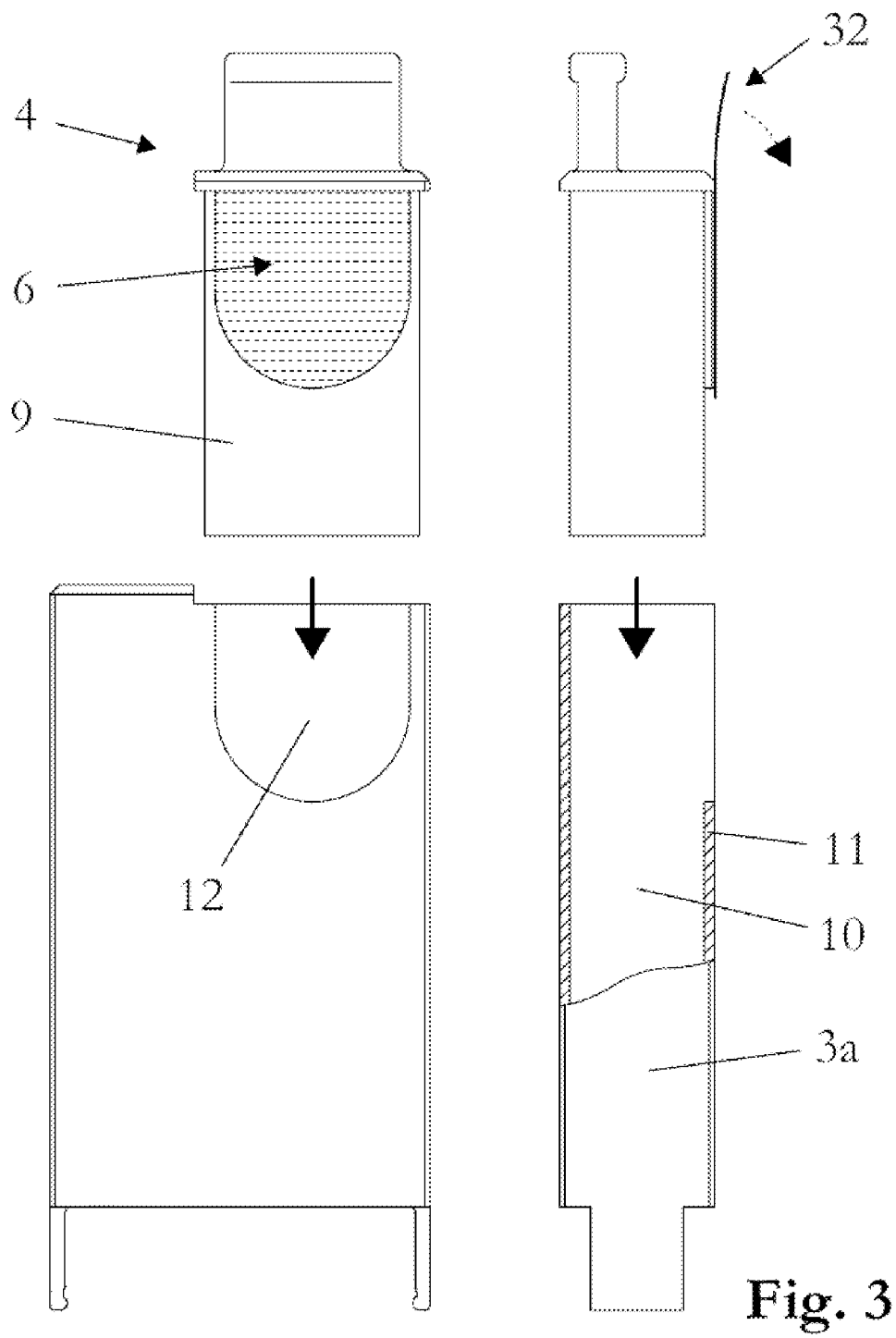
FIG. 3 the replaceable inhaler component with a replaceable mouthpiece in the dismantled condition in different views.

As shown in FIG. 3, the mouthpiece 4 is detachably connected to a housing component 3a. The housing component 3a and parts of the mouthpiece 4 together form the rectangular-shaped housing 3. The mouthpiece 4 forms a hollow cylinder 9 on the side opposite the mouthpiece opening 5, on the cover of which the flavor reservoir 6 is arranged, as is explained in further detail below. The flavor reservoir 6 can thus also be replaced together with the mouthpiece 4. The coupling of the mouthpiece 4 with the housing component 3a is made by the hollow cylinder 9, as the latter is slid into a corresponding opening 10 of the housing component 3a. Furthermore the housing component 3a forms a cover component 11. A U-shaped recess 12 is formed in the cover component 11, which serves, in the course of coupling the mouthpiece 4, to accept the U-shaped flavor reservoir 6 precisely, so that the flavor reservoir 6 can communicate freely with the environment.

Figure 4:
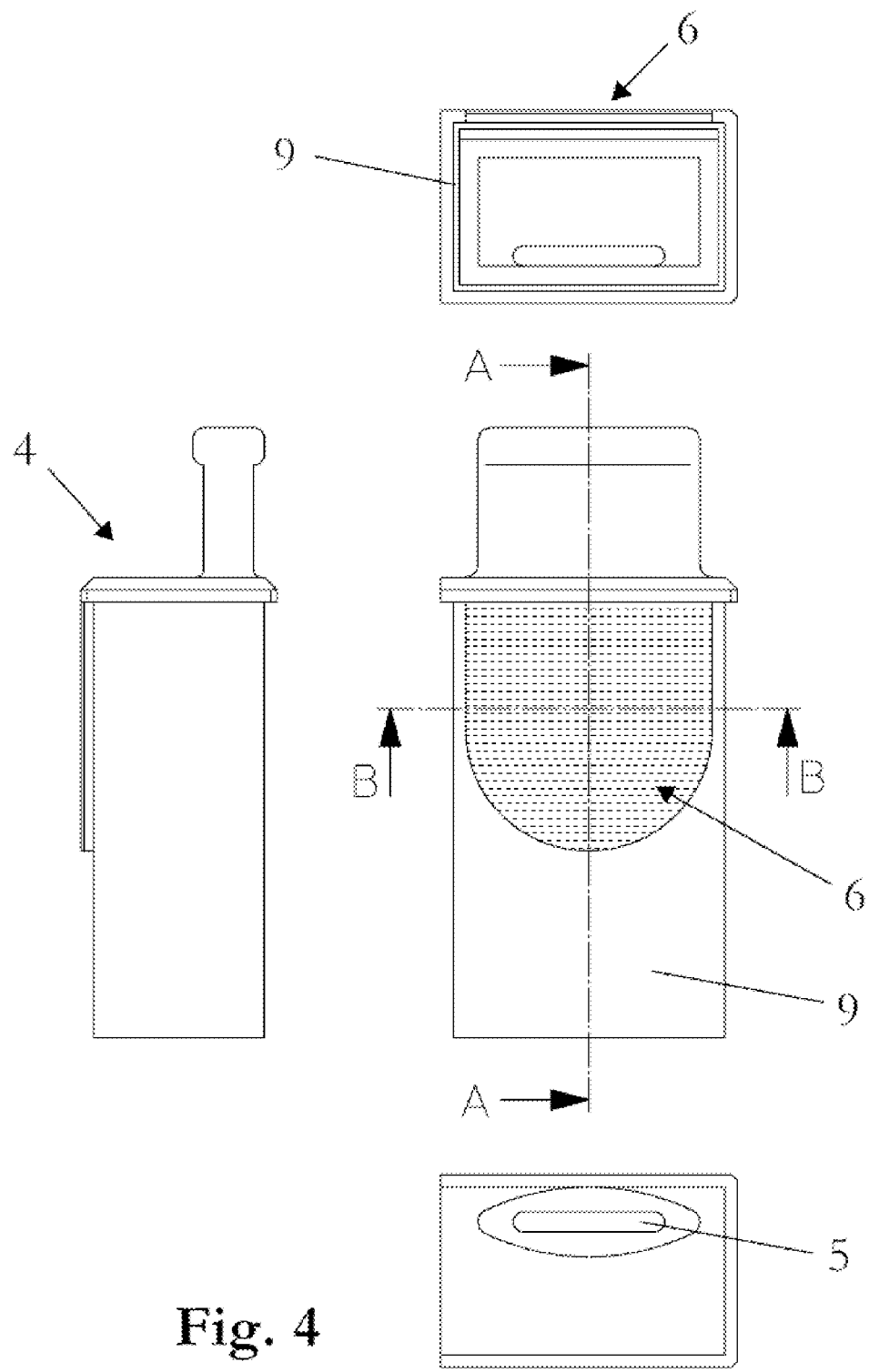
FIG. 4 the replaceable mouthpiece in different views.
Figure 9:
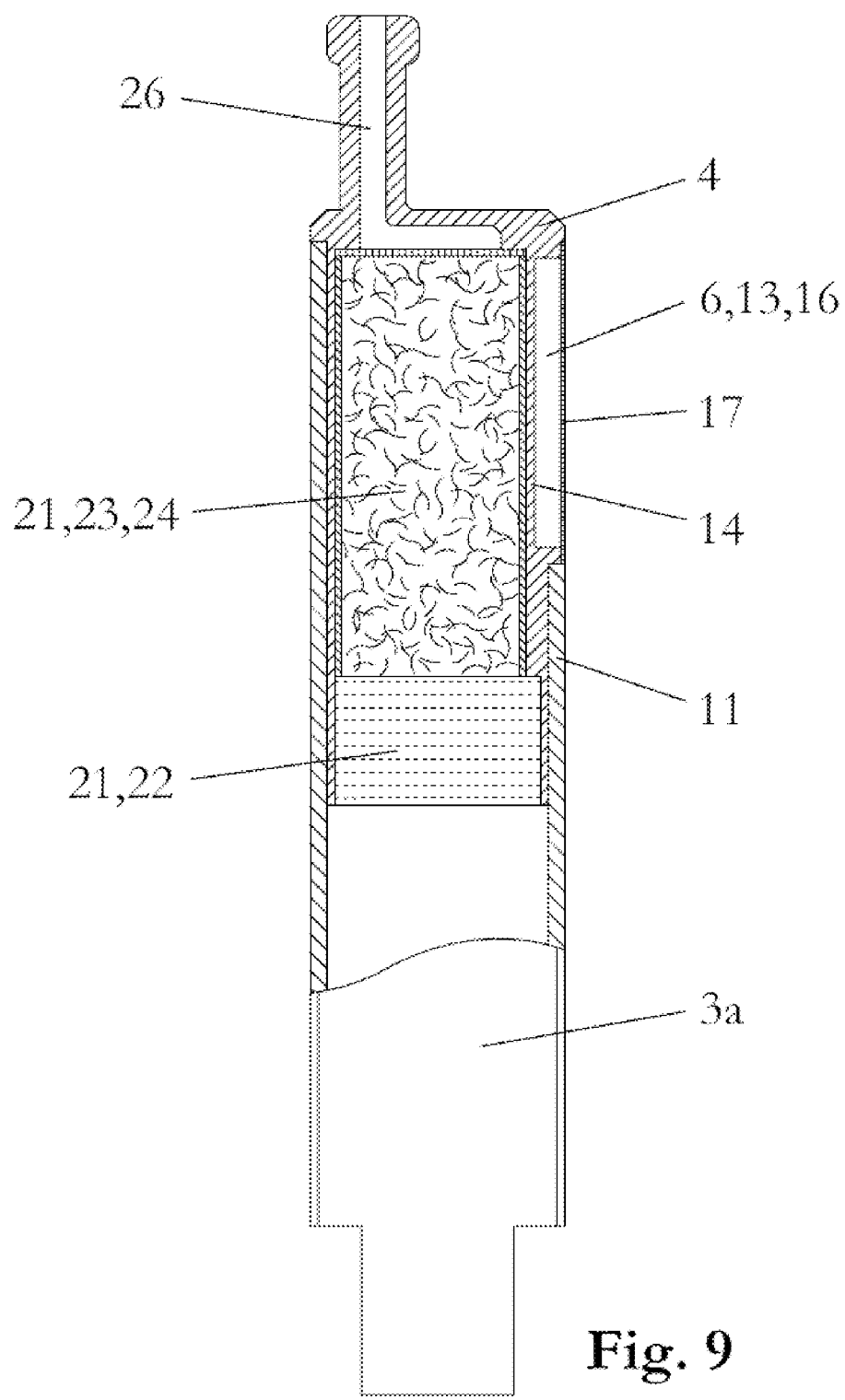
FIG. 9 a partial sectional view of the replaceable inhaler component with mouthpiece attached.

FIGS. 4-6 again show the replaceable mouthpiece 4 on its own in more detail. FIG. 9 shows the mouthpiece 4 coupled with the housing component 3a. As can be inferred from the figures, the hollow cylinder 9 has a rectangular cross section. In the present example, the U-shaped flavor reservoir 6 consists of a flat recess 13 in the cylinder cover 14 of the hollow cylinder 9. The recess 13 is bounded by an elevation 15. The elevation 15 is formed by the hydraulic cylinder cover 14. In the course of coupling the mouthpiece 4 with the housing component 3a, the flavor reservoir 6 and the elevation 15 surrounding the flavor reservoir 6 engage in the recess 12 of the cover component 11 (see FIG. 9).

In the flavor reservoir 6, i.e. in the recess 13, the actual flavor 16 is located, which can be present in liquid, paste-like, solid or gel-like form. The flavor reservoir 6 is bounded to the environment by a gas-permeable diaphragm 17. The diaphragm 17 is fastened to the elevation 15 by welding or fusing and serves several purposes: first of all it prevents the flavoring 16 from running out of the reservoir 6; secondly it throttles and/or controls the flavor release into the environment; thirdly it prevents the penetration of humidity, in particular of rain water, into the flavor reservoir 6; and finally it prevents the user coming into contact with the flavor 16. It is not essential that all the aforementioned effects take place. Thus, for example, it is optionally possible to store the flavoring 16 in an absorbent, wick-like porous body, i.e. to bind it by capillary action as described in more detail below. In this case, the first mentioned effect of the diaphragm 17 would be inapplicable. The gas-permeable diaphragm 17 can, for example, consist of a thermoplastic plastic film, e.g. of polyethylene or of an ethyl vinyl acetate copolymer. The volatile flavor 16 diffuses molecularly through the film. Micro-porous thermoplastic polymer materials appear particularly suitable for the purposes of the present invention. The company Celgard LLC, www.celgard.com, offers such a material, for example in the form of hydrophobic polypropylene diaphragms. The diaphragms are sold under the trade name CELGARD®. EP 836,857 (Eric Jallerat) and U.S. Pat. No. 4,917,301 (Marina A. Munteanu) describe alternative micro-porous polymer materials for the purpose of releasing flavors. The porosity or permeability of the diaphragm 17 must match the specific flavor characteristics (detection threshold, evaporability) of the flavor 16 stored the reservoir 6. Under some circumstances it may also be advantageous to provide several flavor reservoirs independent of each other with different diaphragm characteristics, particularly if the flavor characteristics of the substances contained in the flavor vary significantly. If flavor is present in solid form, for example as fine cut tobacco or as fine tobacco granulates, then the diaphragm 17 can also simply consist of just a fine wire mesh.

Figure 7:
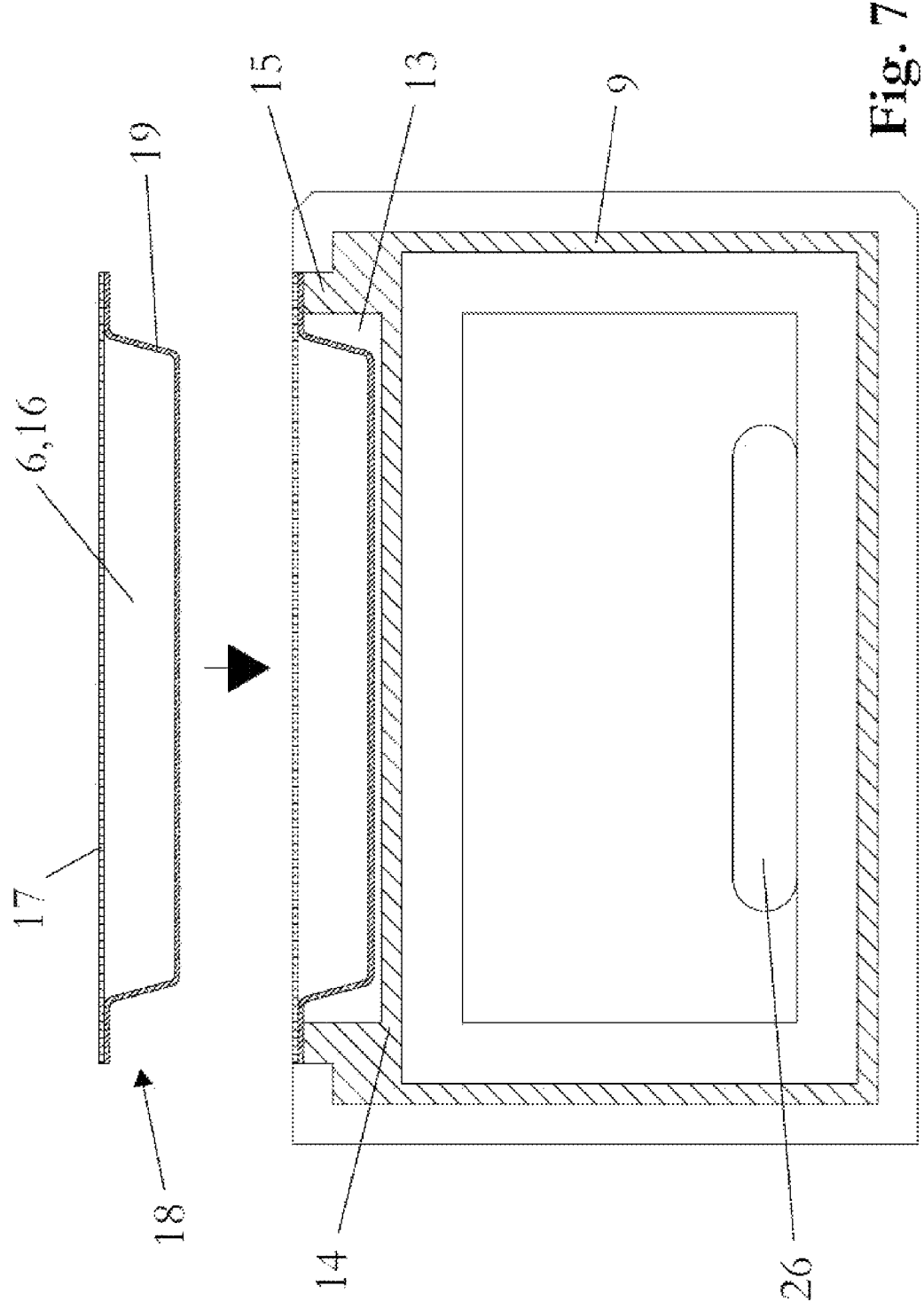

FIG. 7 shows an alternative arrangement of the flavor reservoir 6. In this case the flavor reservoir 6 including the diaphragm 17 is formed from one prefabricated flat flavor packing 18, which can be inserted into a corresponding recess 13 in the cylinder cover 14 of the mouthpiece 4 and to which the elevation 15 is fastened by means of a bond. A flavor packing of this kind has already been proposed earlier in the course of the discussion of U.S. Pat. No. 4,503,851 (Klaus Braunroth). In the patent literature such packings were described for the first time in U.S. Pat. No. 4,094,119 (William E. Sullivan), U.S. Pat. No. 4,145,001 (Robert J. Weyenberg et al.) and U.S. Pat. No. 4,161,283 (Sy Hyman). The flavor packing 18 essentially consists of two parts: on the one hand a gas-permeable diaphragm 17, as described before, and on the other hand an impermeable film 19, consisting, for example, a plastic laminate or of an aluminum-plastic laminate. The impermeable film 19 is welded or fused around the margin with the diaphragm 17 and thus forms the flavor reservoir 6 in the interior. The use of a prefabricated and filled flavor packing 18 in an inhaler component in accordance with the invention 2 and/or in a replaceable mouthpiece 4 in accordance with the invention offers cost advantages during mass production of the same.

Figure 8:
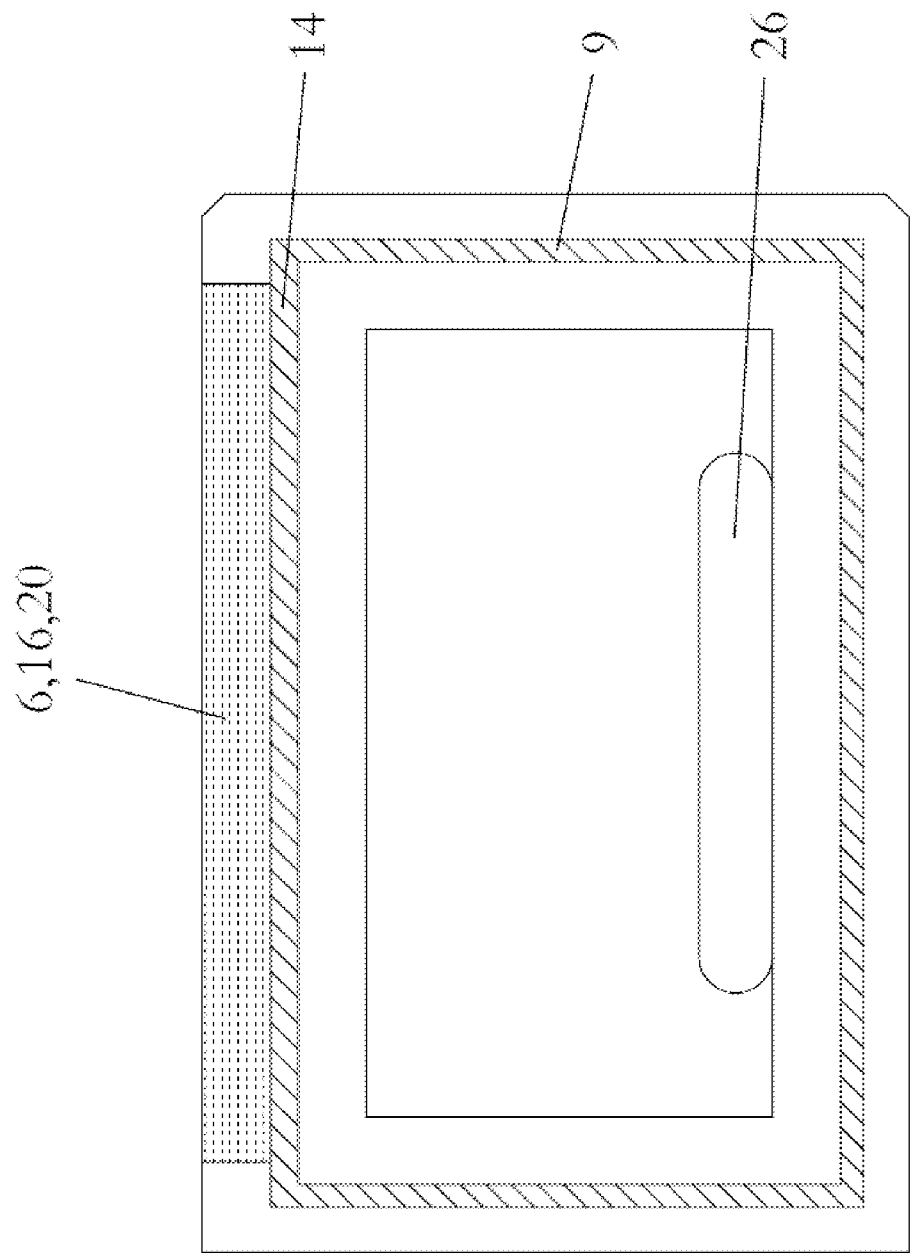

FIG. 8 shows a further alternative arrangement of the flavor reservoir 6. The flavor reservoir 6 in this case is formed from a porous body 20 with the flavor 16 absorbed in its pores. The plate-shaped porous body 20 consists of an absorbent, wick-like material and is fastened by means of a bond to the cylindrical cover 14 of the mouthpiece 4. The material of the porous body 20 should be as shape-retaining as possible and to a large extent inert to the flavor 16. Suitable for this are:

Fibrous moldings of natural or chemical fibers, bonded by heat or with the aid of a binder; the company Filtrona Richmond Inc., www.filtronaporoustechnologies.com, specializes in the production of such GRP components, produced both by means of triacetin-bonded cellulose acetate fibers and thermally bonded polyolefin and polyester fibers;

Open-pored sintered molded articles, e.g. porous-sintered polyethylene or polypropylene material from the company Porex Technologies, www.porex.com;

Foam material, in particular metal foam; the company Mitsubishi Materials Corporation, www.mmc.co.jp, has such a foam material of stainless steel (e.g. AISI 316L) in thicknesses of up to 2 mm and with a porosity >90% in their range as standard.

Paste-like and solid flavors can be dissolved or dispersed beforehand in a suitable solvent, so that they can be more easily absorbed by the porous body 20. In the example in accordance with FIG. 8 the flavor reservoir 6 and/or the porous body 20 communicate directly with the environment. A diaphragm is not envisaged. Such a simple arrangement is particularly recommended when using flavors of low volatility and/or high odor thresholds. The invention is naturally not limited to this special case. The porous body 20 could rather be used in a recess 13 exactly the same as in FIG. 6, or in a flavor packing 18 in accordance with FIG. 7.

Figure 5:
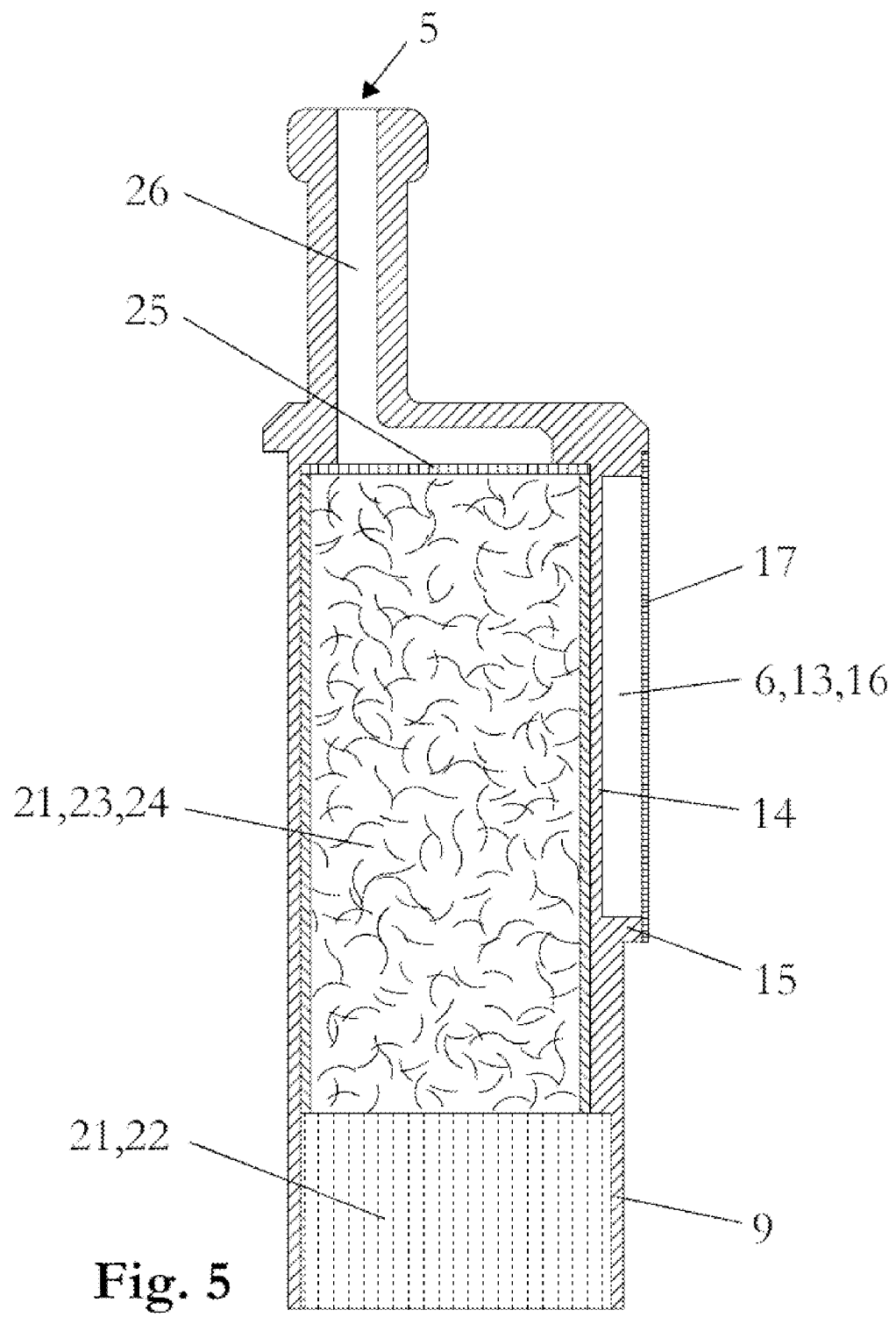
FIG. 5 a cutaway view of the replaceable mouthpiece along the line A-A in FIG. 4.
Figure 6:
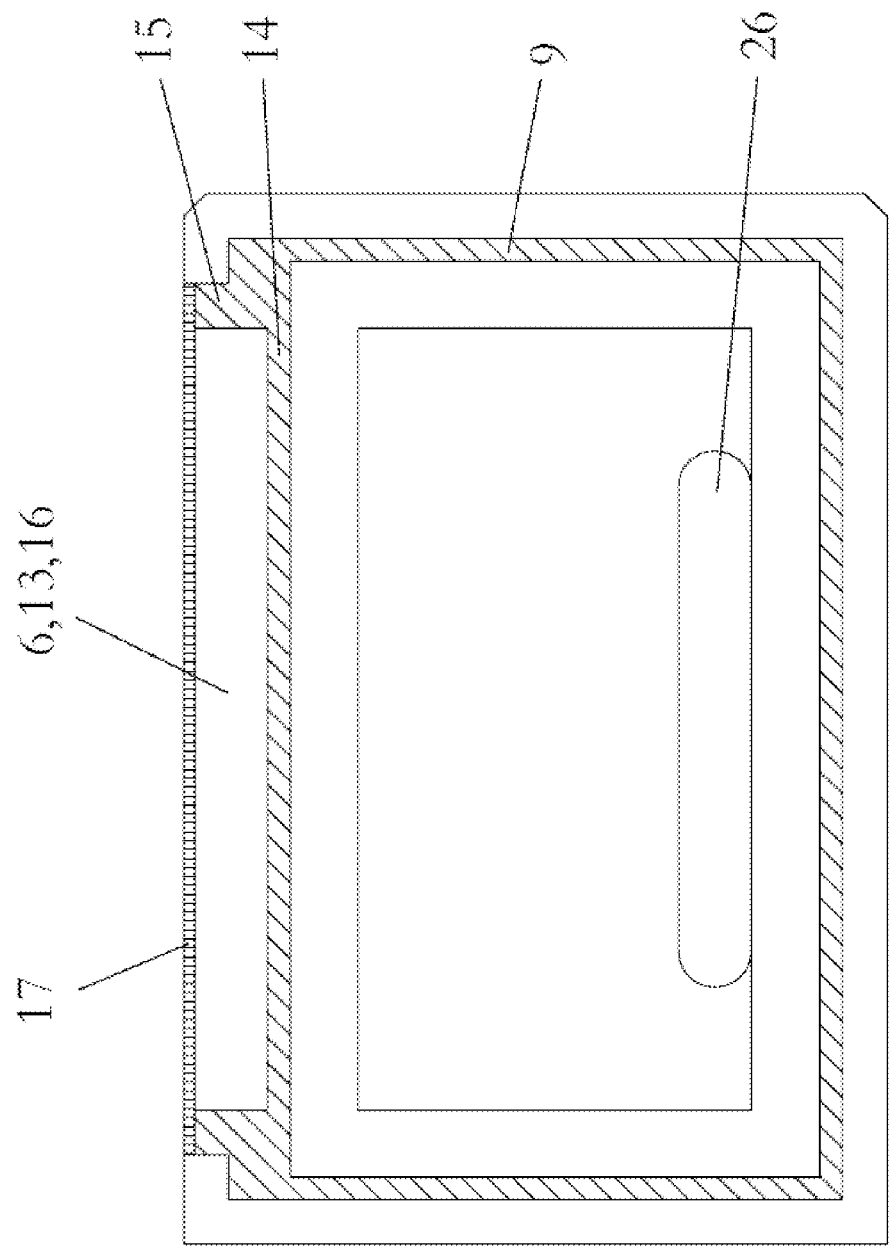
FIGS. 6-8 in each case a cutaway view of the replaceable mouthpiece along the line B-B in FIG. 4; different types of flavor reservoir.

As shown in FIG. 5 and FIG. 9, a cooler 21 through which the inhalable medium can flow is located within the hollow cylinder 9. The cooler in accordance with the present example, designed particularly for cooling a vapor-air mixture and/or condensation aerosol formed by evaporating a highly diluted nicotine solution. The cooler 21 is constructed in two stages and consists of a pre-cooler 22 and a tobacco filling 23 following it. The pre-cooler 22 forms the first cooler stage and has the task of pre-cooling the vapor-air mixture and/or condensation aerosol as effectively and completely as possible before it reaches the tobacco filling 23. The pre-cooler reduces loading of solvent condensate on the tobacco filling 23. Excessive loading of the tobacco filling 23 with condensate is known to affect the flavoring effect of the same unfavorably. The pre-cooler 22 can, for example, consist of a synthetic fiber felt. The company Freudenberg Vliesstoffe KG, www.freudenberg-filter.com, offers such a material in the form of mats/panels under the designation Viledon® filter mats. The material can be made to customer specifications. In particular the material properties can be co-ordinated in such a way that the final product is, as far as possible, permeable to the fine particles of the condensation aerosol produced. The mats/panels are made from polyolefin fibers (PE, PP) or polyester fibers and can be processed by stamping machines. The tobacco filling 23 is available as prefabricated packing and consists of a paper-wrapped tobacco strand 24, which is advantageously produced from a continuous strand. The tobacco strand 24 and the pre-cooler 22 are pushed into the hollow cylinder 9. The pre-cooler 22 is fastened in the hollow cylinder 9 by means of a bond, to which the tobacco strand 24 is also indirectly fixed. On the mouthpiece side, the tobacco filling 23 is retained by a wire mesh 25, which prevents the packing reaching the mouthpiece channel 26 or the oral cavity of the user. The pre-cooler 22 and the tobacco strand 24 together with the mouthpiece 4 thus form a structural unit, which is replaceable together with the flavor reservoir 6. The tobacco strand 24, like cigarettes, can optionally be additionally flavored and/or mentholated, where similar procedures can be used.

Figure 10A:
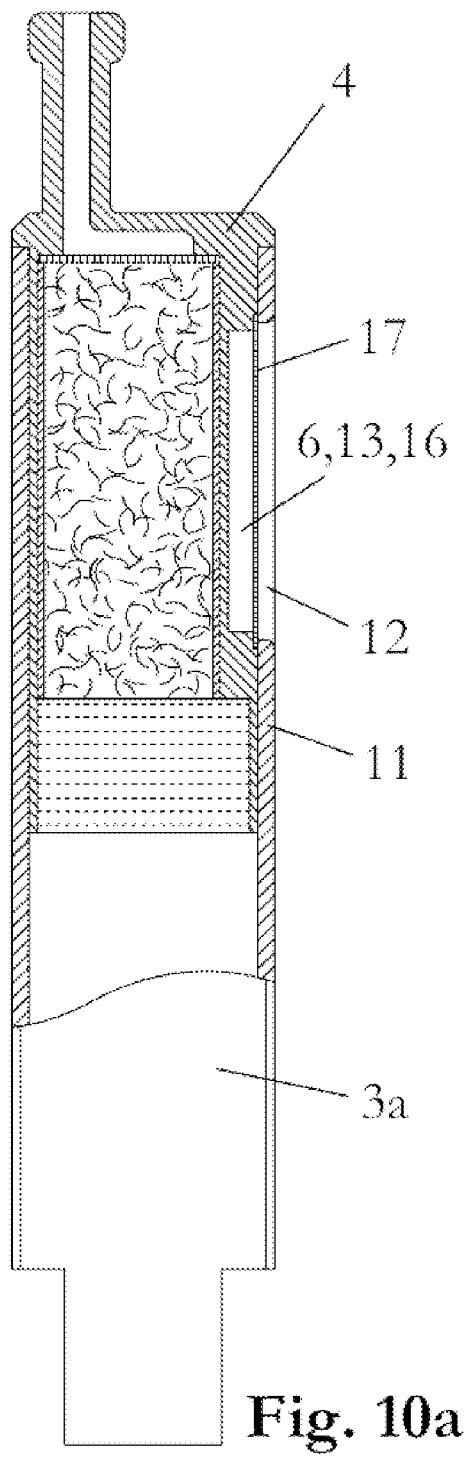
FIGS. 10a and 10b in each case a partial sectional view of the replaceable inhaler component with mouthpiece attached; two alternative embodiments.
Figure 10B:
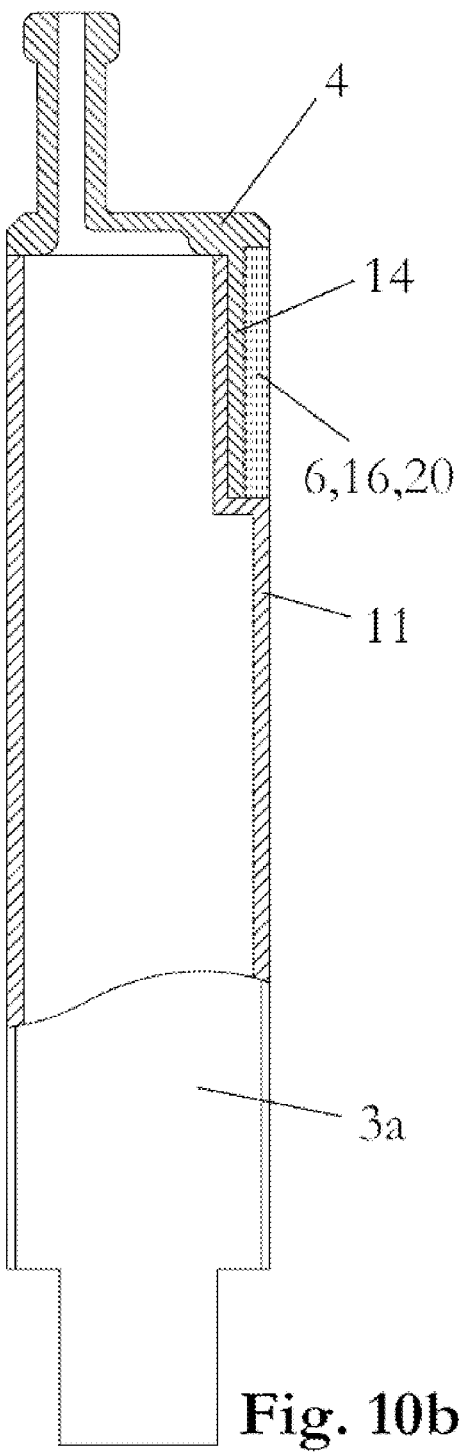

FIG. 10a and FIG. 10b show two examples of alternative arrangements of the inhaler component 2 with coupled mouthpiece 4. The arrangement in accordance with FIG. 10a, like the example previously shown (see FIG. 3 and FIG. 9), has a recess 12 in the cover component 11. Here, however, the flavor reservoir 6 does not engage in the recess 12, but is displaced somewhat towards the interior and communicates with the environment via the recess 12, as if through a window. The example in accordance with FIG. 10b shows an arrangement in which the mouthpiece 4 forms a cover part 14, which the cover component 11 partly overlaps in the region of the flavor reservoir 6. In principle, a self-supporting arrangement would also be possible, in which the flavor reservoir 6 itself forms cover part 14 and directly overlaps the cover component 11. Both alternative examples likewise make relatively compact overall arrangements possible.

Figure 11:
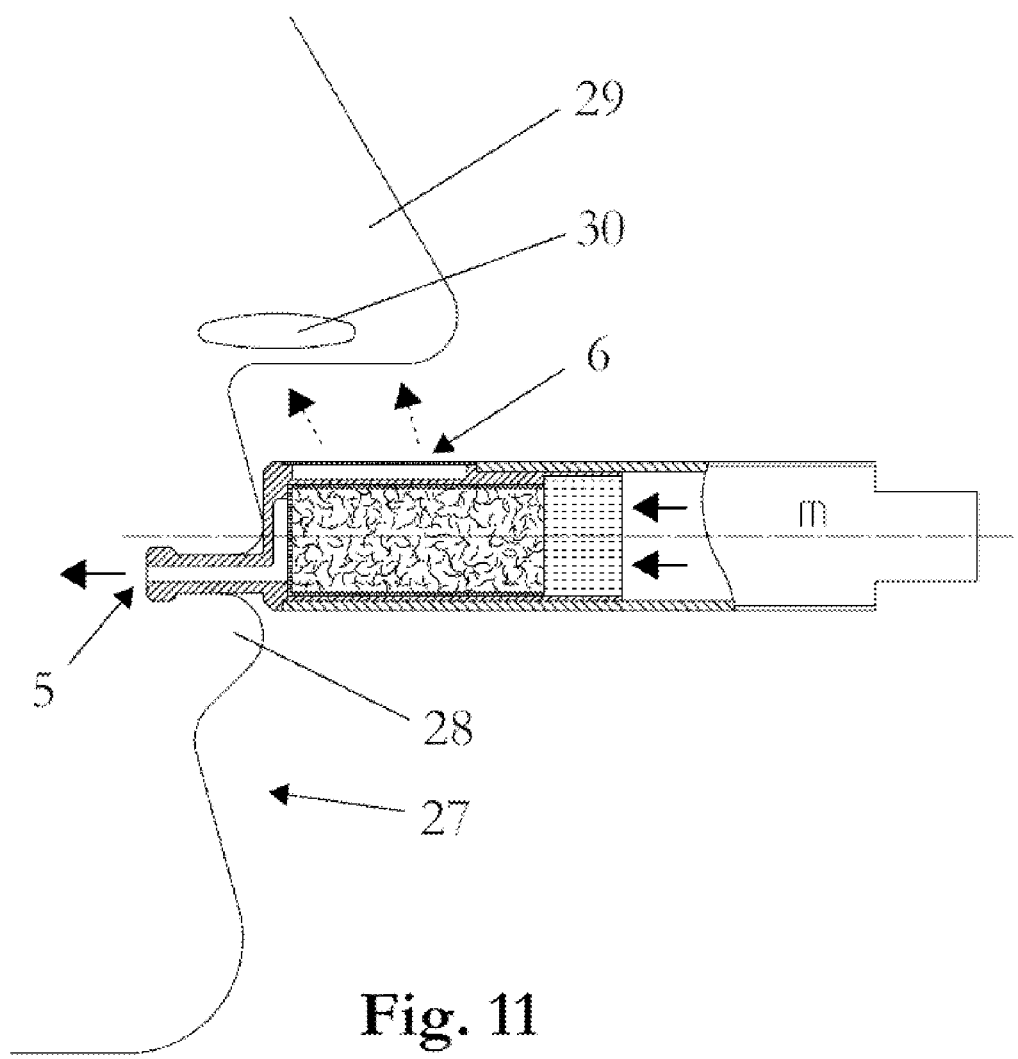
FIG. 11 the replaceable inhaler component in accordance with FIG. 9 in position for use.

Finally, FIG. 11 shows the inhaler component 2 in its position of use. The flow of the inhalable medium is symbolized by solid arrows; the release of the flavoring is characterized by broken arrows. As can be clearly seen, the two material flows do not affect one other. The inhalable medium preferably consists of a nicotine-containing vapor-air mixture and/or aerosol. The origin of the inhalable medium and/or the nature of the formation of the same within the inhaler component 2 is not of relevance for the object of the invention and consequently also does not need to be defined in more detail in this context.

A user 27 holds the tobacco-pipe-like, flat mouthpiece end of the mouthpiece 4 between his lips 28. The flat mouthpiece end is aligned parallel to the plate-like flavor reservoir 6. This therefore ensures that the flavor reservoir 6 is always positioned exactly opposite the nose 29 and/or opposite the nostrils 30 of the user 27. Furthermore the tobacco-pipe-like mouthpiece end is not set centrally, but displaced on the front face of the housing 3, so that the mouthpiece opening 5 and the flavor reservoir 6 are on opposite sides of the housing centre plane m. This constructional feature has the effect that the flavor reservoir 6 moves as close as possible to the nostrils 30, without, however, extending beyond the housing surface of the inhaler component 2, so that the inhaler remains easily manageable and also meets aesthetic requirements. The short distance from the flavor reservoir 6 to the nostrils 30 makes a high material transfer efficiency possible, which means that a comparatively large part of the overall quantity of flavor released can actually reach the nostrils 30 and exert an olfactory effect.

Figure 12:
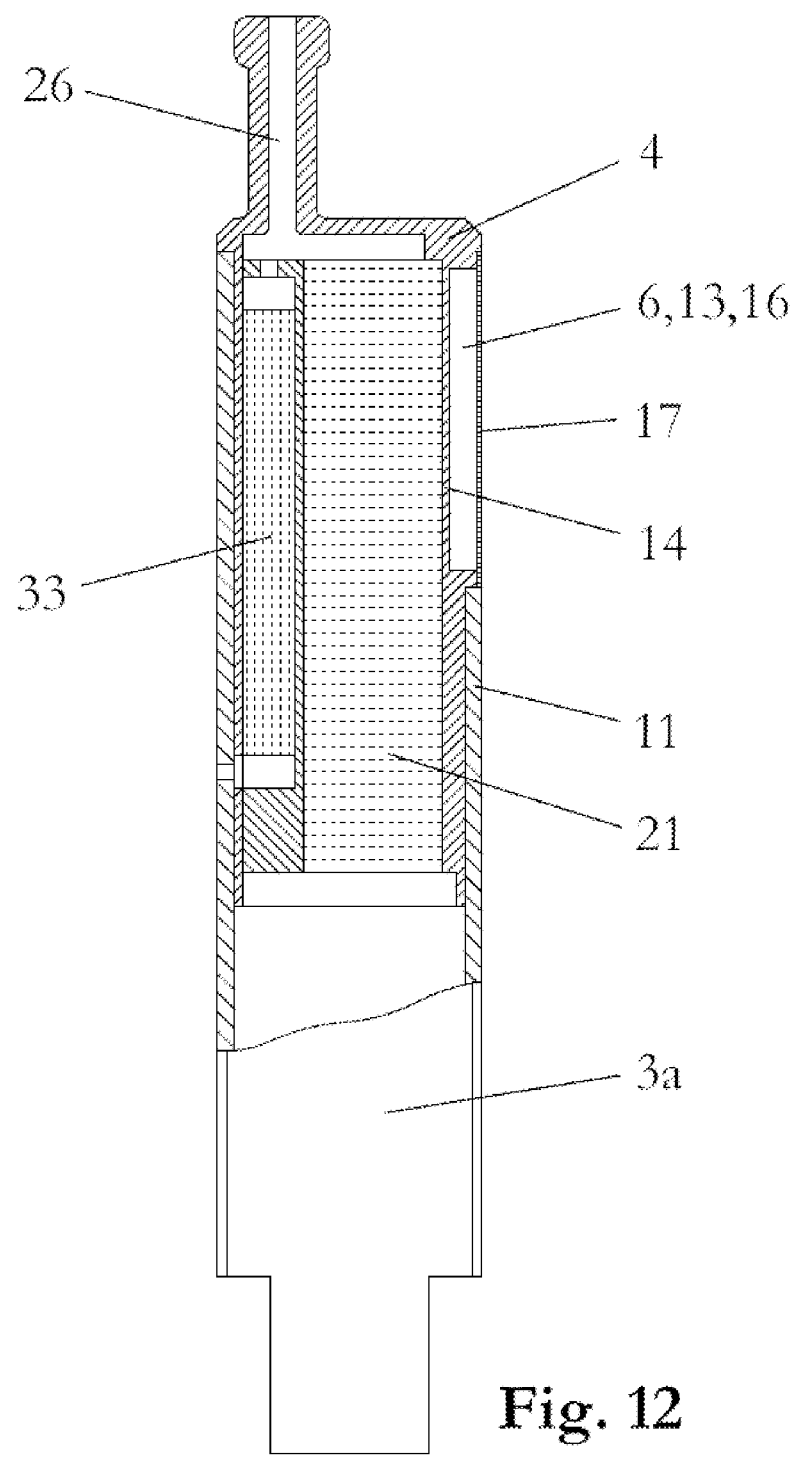
FIG. 12 a partial sectional view of the replaceable inhaler component with mouthpiece attached in a further extended variant.
Figure 13:
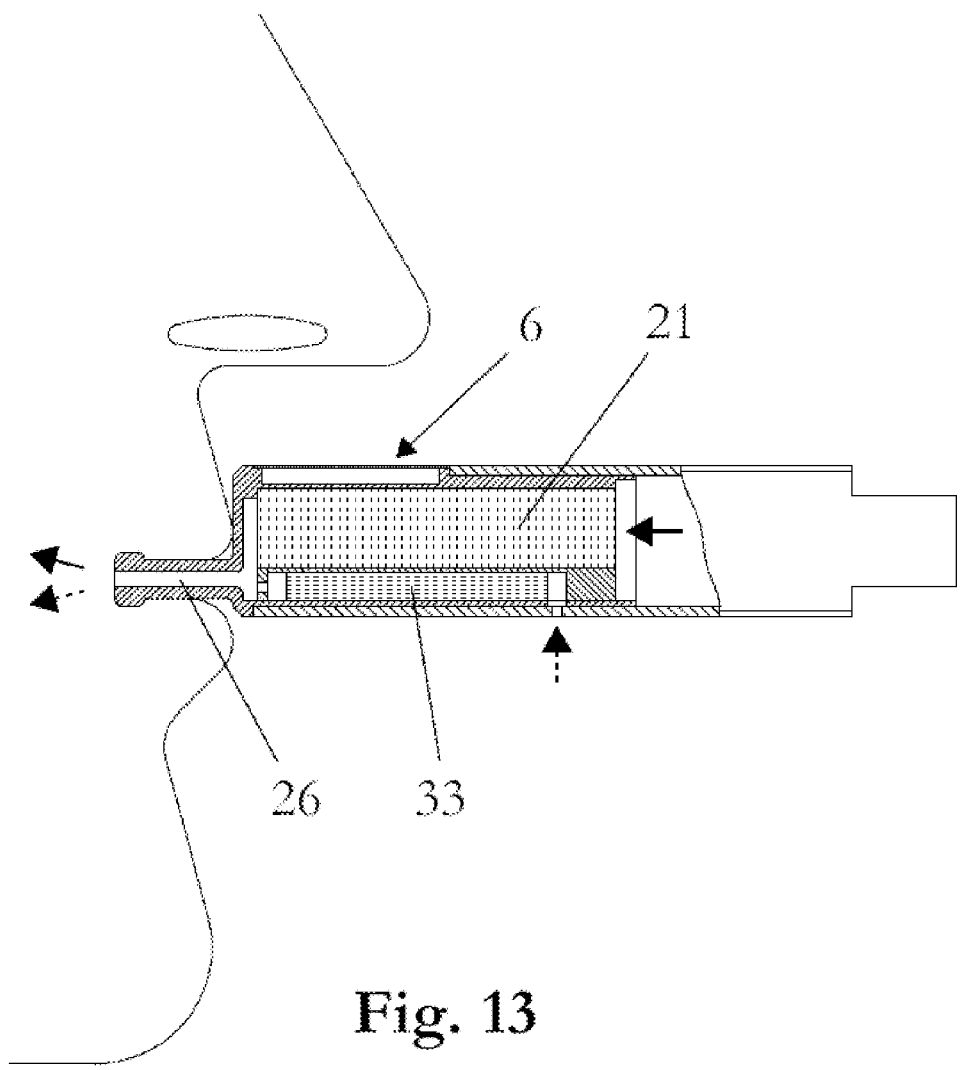
FIG. 13 the replaceable inhaler component in accordance with FIG. 12 in position for use.

FIG. 12 shows a further variation of the replaceable inhaler component. This differs from the embodiment in accordance with FIG. 9 in that a separate flavoring reservoir 33 is provided beside the cooler 21. The flavoring reservoir 33 forms a structural unit, which together with the flavor reservoir 6 is again replaceable together with the cooler 21 and the mouthpiece 4. As shown in FIG. 13, the flavoring and cooling of the inhalable medium occur spatially separate from one another, where two material flows occur: first of all, a flow of air through the flavoring reservoir 33, which is fed from the environment (symbolized by broken arrows), and secondly, the actual mainstream through the cooler 21, which is restricted to the vapor-air mixture and/or aerosol (symbolized by solid arrows). The two material flows unite far downstream in the input area to the mouthpiece channel 26 and finally arrive together in the oral cavity of the user. The large separation of the two material flows prevents aerosol particles in the flavoring reservoir 33 or condensate formed from the vapor phase, particularly solvent condensate, from settling out. These separations could severely disturb the release of the flavoring. The two material flows are brought about by the suction pressure produced by the user at the mouthpiece. Consequently, the flow resistances of the flavoring reservoir 33 on the one hand and of the cooler 21 on the other hand, as well as, if necessary, any other components through which there is a flow, must be matched to each other in such a way that the desired resistance characteristic, e.g. that of a cigarette, and the desired flow rates are achieved.

Since in the specific example no flavoring effect is demanded of the cooler 21, it is obvious, for the sake of simplicity, to implement these as a single-step. As cooling material, synthetic fiber felt, as already described, can be used. The flavoring reservoir 33 can consist, for example, of a permeable highly porous wadding, where it is particularly advantageous if the wadding contains tobacco or consists of tobacco. Suitable tobaccos are, in particular, dried fermented tobacco, reconstituted tobacco, expanded tobacco or mixtures of the same. It is particularly advantageous if the tobacco is present as cut tobacco, preferably fine cut tobacco, or as fine granulates or tobacco flour. The large surface of these forms of tobacco supports the release of the flavoring contained in the tobacco. Alternatively, the flavoring reservoir 33 can also consist of an inert wadding or other open-pored substrate, the surface of which is coated with the flavoring. The coating can, for example, contain a tobacco smoke condensate or a tobacco extract or a volatile aromatic fraction of the aforementioned material mixtures or tobacco flour. The coating can alternatively or additionally contain menthol or ethereal oil containing it.

WO 2010/095659 (Takeuchi Manabu et al.) and WO 2010/095660 (Yamada Manabu et al.) describe detailed examples of air-permeated flavoring reservoirs. Inhalers equipped with such flavoring reservoirs have meanwhile also already appeared on the market and been sold by Japan Tobacco Inc., www.jt.com, under the label name Zero-Style®.

Since the flavor release itself in the example in accordance with FIG. 13 does not differ from one in accordance with FIG. 11, a repeated representation of these connections has been omitted.

The invention is naturally not limited to the examples illustrated by means of the drawings and can naturally be further developed appropriately in accordance with the particular requirements. It would thus be conceivable, for example, to arrange a sliding cover on the outside of the housing of the inhaler component 2, so as to be able with its assistance effectively to adjust the surface of the flavor reservoir 6 communicating with the environment, giving the user the ability to adjust the flavor release to his personal needs. The sliding cover could also be used to close the flavor reservoir 6 completely, for example during periods when the inhaler is out of use for long periods. Alternatively one could also provide a cap 31 to be employed over the front surface of the inhaler component 2 and over the mouthpiece 4 and outside the housing 3 (see FIG. 1), which seals not only the flavor reservoir 6, but at the same time the mouthpiece opening 5. In order to prevent an escape of the flavoring 16 before the actual use of the flavor reservoir 6, the flavor reservoir 6 must be suitably packed. Such a packing can be effected in a simple manner by means of a self-adhesive impermeable protective plastic film 32, which covers the surface of the flavor reservoir 6 (see FIG. 3; broken arrow). The replaceable mouthpiece 4 as such should be packaged for marketing in a hermetically sealed foil pack.

REFERENCE SYMBOL LIST

1 inhaler part
2 inhaler component
3 housing
3a housing component
4 mouthpiece
5 mouthpiece opening
6 flavor reservoir
7 latching hook
8 detent
9 hollow cylinder
10 opening
11 cover component; first cover part
12 cutout
13 recess
14 hydraulic cylinder cover; second cover part
15 elevation
16 flavor
17 gas-permeable diaphragm
18 flavor packing
19 impermeable film
20 porous body
21 cooler
22 pre-cooler
23 tobacco filling
24 tobacco strand
25 wire mesh
26 mouthpiece channel
27 user
28 lips
29 nose
30 nostrils
31 cap
32 protective plastic film
33 flavoring reservoir

The invention claimed is:
1. Inhaler component, comprising:
a housing, with a housing cover, extending in a longitudinal direction;
a mouthpiece with a mouthpiece opening for supplying an inhalable medium provided by the inhaler component into the oral cavity of a user; and
a flavor reservoir communicable with the environment by diffusion, containing a flavor, wherein the flavor reservoir is formed from a porous body,
wherein the mouthpiece additionally comprises a flavoring reservoir through which the inhalable medium can flow to enrich the inhalable medium with flavoring, and
wherein the inhalable medium is a condensation aerosol, and wherein the flavor reservoir longitudinally overlaps the flavoring reservoir.

2. Inhaler component in accordance with claim 1, wherein the flavor reservoir is inseparably connected with the mouthpiece.

3. Inhaler component in accordance with claim 1, wherein the flavor reservoir is present in a recess in the mouthpiece.

4. Inhaler component in accordance with claim 1, wherein a wall of the mouthpiece conducting the inhalable medium is coated with a flavoring material.

5. Inhaler component in accordance with claim 1, wherein the flavor in the flavor reservoir contains tobacco.

6. Inhaler component in accordance with claim 5, wherein the tobacco is present as at least one of cut tobacco, fine cut tobacco, fine granulates, or tobacco flour.

7. Inhaler component in accordance with claim 1, wherein the flavor in the flavoring reservoir contains tobacco.

8. Inhaler component in accordance with claim 1, wherein the flavoring reservoir contains at least one of a tobacco smoke condensate, a tobacco extract, or a volatile aromatic fraction of a material mixture of a tobacco smoke condensate and a tobacco extract, but is essentially nicotine-free.

9. Inhaler component in accordance with claim 1, wherein the flavor in the flavor reservoir contains at least one of a tobacco smoke condensate, a tobacco extract, or a volatile aromatic fraction of a material mixture of a tobacco smoke condensate and a tobacco extract, but the flavor is essentially nicotine-free.

10. Inhaler component in accordance with claim 1, wherein the flavor in the flavor reservoir contains at least one volatile acid.

11. Inhaler component in accordance with claim 10, wherein the proportion of all volatile acids in the flavor is a total of more than 5% by weight.

12. Inhaler component in accordance with claim 1, wherein the flavor in the flavor reservoir contains at least one of menthol or peppermint oil.

13. Inhaler component in accordance with claim 1, wherein the flavoring reservoir contains at least one of menthol or peppermint oil.

14. Inhaler component in accordance with claim 1, further comprising a housing center plane m that divides the housing in a cover direction into two approximately equal-sized parts, wherein the mouthpiece opening and the flavor reservoir are arranged on opposite sides of the housing center plane m.

15. Inhaler component in accordance with claim 1, further comprising a removable cap employed over a front surface of the inhaler component and over the mouthpiece, and outside the housing.

16. Inhaler component in accordance with claim 1, wherein the porous body comprises chemical fibers.

17. Inhaler component in accordance with claim 16, wherein the chemical fibers comprise cellulose acetate fibers.

18. Inhaler comprising an inhaler component in accordance with claim 1, wherein the inhaler further comprises a rechargeable battery.

* * * * *